United States Patent [19]

Corey

[11] 4,185,618
[45] Jan. 29, 1980

[54] PROMOTION OF FIBROUS TISSUE GROWTH IN FALLOPIAN TUBES FOR FEMALE STERILIZATION

[75] Inventor: Harold Corey, Ringwood, N.J.

[73] Assignee: Population Research, Inc., Clearwater, Fla.

[21] Appl. No.: 919,267

[22] Filed: Jun. 26, 1978

Related U.S. Application Data

[63] Continuation-in-part of Ser. No. 828,736, Aug. 29, 1977, abandoned, which is a continuation of Ser. No. 646,649, Jan. 5, 1976, abandoned.

[51] Int. Cl.$^2$ .................... A61B 19/00; A61K 31/78
[52] U.S. Cl. .................... 128/1 R; 106/74; 106/162; 106/194; 106/205; 106/238; 128/130; 128/216; 128/235; 128/260; 424/78; 424/81; 424/361; 424/362; 424/363
[58] Field of Search .................... 424/78, 81, 361, 362, 424/363; 128/130, 1 R, 216, 235, 260; 106/74, 162, 194, 205, 238

[56] References Cited

U.S. PATENT DOCUMENTS

| | | | |
|---|---|---|---|
| 3,483,870 | 12/1969 | Coover et al. | 424/81 X |
| 3,485,915 | 12/1969 | Gerstein et al. | 424/81 |
| 3,496,938 | 2/1970 | Furuse et al. | 128/271 |
| 3,551,556 | 12/1970 | Kliment et al. | 424/81 X |
| 3,563,978 | 2/1971 | Ochs | 424/78 X |
| 3,577,522 | 5/1971 | Hymes | 424/78 |
| 3,590,125 | 6/1971 | Hymes | 424/78 |
| 3,639,575 | 2/1972 | Schmolka | 424/78 |
| 3,640,741 | 2/1972 | Etes | 424/361 X |
| 3,644,650 | 2/1972 | Sabatelli et al. | 424/78 X |
| 3,822,702 | 7/1974 | Bolduc et al. | 128/1 R X |
| 3,865,108 | 2/1975 | Hartop | 128/260 |
| 3,948,259 | 4/1976 | Bolduc et al. | 128/1 R X |

OTHER PUBLICATIONS

Ouer, Annals of Allergy, vol. 9, pp. 346-353, May-Jun. 1951.
Pitkin, Obstetrics and Gynecology, vol. 28, No. 5, pp. 680-683, Nov. 1966.
Homsy, I; J. Biomed. Mater. Res., vol. 4, pp. 341-356, 1970.
Zipper et al., Fertility and Sterility, vol. 21, No. 8, pp. 581-589, Aug. 1970.
Rakshit, Obstetrics and Gynecology of India, vol. 20, pp. 618-624, 1970.
Wyandotte Corporation, Pluronic Polyols, Toxicity and Irritation Data—3rd Ed., Revised, 20 pages, 1971.
Ringrose, Obstetrics and Gynecology, vol. 42, No. 1, pp. 151-155, Jul. 1973.
Homsy, II, Orthopedic Clinics of North America, vol. 4, No. 2, pp. 295-311, Apr. 1973.
Davidson et al., Contraception, vol. 4, No. 4, pp. 333-339, Apr. 1973.
Lin et al., American Journal of Obstetrics and Gynecology, vol. 116, No. 2, pp. 167-174, May 1973.

*Primary Examiner*—Bernard Helfin
*Assistant Examiner*—Vera C. Clarke
*Attorney, Agent, or Firm*—Schroeder, Siegfried, Ryan, Vidas, Steffey & Arrett

[57] ABSTRACT

A composition and method of using same is disclosed for the permanent sterilization of female subjects without the need for expensive surgery or highly skilled personnel. The composition comprises a gel-forming carrier substance which sets-up on introduction into the fallopian tubes and holds in place a tissue fibrosing promoting material carried thereby for a period of time to cause fibrous tissue growth which closes the fallopian tubes and results in sterilization.

25 Claims, No Drawings

PROMOTION OF FIBROUS TISSUE GROWTH IN FALLOPIAN TUBES FOR FEMALE STERILIZATION

This application is a continuation-in-part of application Ser. No. 828,736, filed Aug. 29, 1977 now abandoned, and assigned to the same assignee. Application Ser. No. 828,736 is a continuation application of Ser. No. 646,649, filed Jan. 5, 1976, now abandoned, also assigned to the same assignee.

The present invention is directed to compositions for use in the permanent sterilization of female subjects, including human females as well as female animals having fallopian tubes or the like. The invention is also directed to a method of effecting the sterilization.

BACKGROUND OF THE INVENTION

Various birth control methods have been utilized in the past in attempts to prevent undesired conception. One technique which has long been recognized as a birth control method is to prevent the ovulation on the part of the female so that the ova is not available to combine with the sperm. This can be accomplished surgically by tieing off the fallopian tubes. This procedure has disadvantages, among which are that it requires highly skilled personnel to perform the necessary operation and also requires expensive hospital facilities in order to insure the safety of the patient.

It has long been proposed to use various kinds of chemical agents injected into the upper part of the uterus and the fallopian tubes to bring about sterilization through the scarifying of the tissue of the walls of the fallopian tubes. Techniques have been proposed which in effect burn the tissue through the use of high temperatures or chemical irritants on the tissue so that a growth of fibrous tissue acts to block the fallopian tube. It has also been proposed to place a physical block within the fallopian tubes such as a piece of inert plastic material.

Varying degrees of success have been achieved through each of these techniques. One such technique has been the use of a methylcyanoacrylate resin which is injected through the use of a special apparatus into the fallopian tube where, due to the properties of the fluid plastic, it then sets up. The hardened plastic causes an irritation to the tissue of the fallopian tube and as the methylcyanoacrylate is absorbed by the body, it is replaced by fibrous tissue bringing about a permanent closure. This latter technique and apparatus suitable for its placement is described in U.S. Pat. No. 3,822,702, which patent is assigned to the same assignee as the present invention.

THE INVENTION

The present invention includes the use of many of the fibrous tissue growth promoting agents of the prior art. For sake of brevity, these fibrous tissue growth promoting agents will also sometimes be referred to therein below as tissue active chemicals or agents. The invention constitutes an improvement over the prior art in the formulation and use of gel or gel producing carriers for the tissue active chemicals. Such gel carriers provide at least two important advantages over the prior art techniques of utilization of such tissue active materials. First, the gels act to retain the active chemical agent in the fallopian tube during the critical time period when the desired effect is being created by the response of the tissue to the presence of the chemicals within the fallopian tube. Second, the micelle structure of the gel is believed to bring about a controlled release of the tissue active chemicals to the tissue surface at a rate which is harmonious with maximizing of fibrous tissue growth and minimizing of the possibilities of adverse tissue damage.

The invention constitutes an improvement over other approaches that have been utilized to attempt to retain the tissue active chemicals in position in the fallopian tubes for the period of time necessary to bring about the desired blockage. Prior investigators have made some use of viscosity increasing agents, apparently recognizing that there is a tendency for the active chemical material to flow outwardly from the fallopian tubes and thus fail to bring about the desired growth promotion of tissue to block the fallopian tube. Frequent reference is made in the literature to the need for more than one application of the tissue active material. Through the use of the carrier gel agents of the present invention, the active chemicals are retained in position within the fallopian tube for a period sufficient to insure complete blockage of the tube by the promotion of growth of fibrous tissue.

There are several different types and classes of gels which are usable within the concept of the present invention. The first and a preferred type of gels are those which become gels through a change in temperature. More particularly, reference is made to those gel-forming substances which are liquid at normal room temperature but which form gel structures as temperature is raised. Also, this type includes gel-forming substances which are liquid at temperatures above body temperature but which set-up as gels when the temperature is lowered following introduction into the body of the subject. The second type of gelling substances are those which become gels under the influence of being mixed with gel promoting agents such as certain metal ions, for example, $Al^{+3}$, $B^{+3}$, $Fe^{+3}$, etc. A third type of gel usable in the invention includes those gels which are gels prior to injection into the subject and which are at least momentarily converted to fluids or semi-fluids by the shear forces of the injection. Upon a cessation of the shear forces the gel structure is reconstituted. While characterized as a third type of gel, this type includes gels of each of the other types and differs primarily in the state of the carrier substance at the time it is injected into the subject's fallopian tubes. In certain cases, where the gel is to be introduced by first undergoing a fluidization or semi-fluidization by introduction of shear stresses during the injection cycle, relatively high stresses may be required.

In general, it can be seen that the gel-forming carrier substance contemplated for use with this invention, whatever its form initially, must form a gel in situ following introduction or insertion into the fallopian tubes. Preferably, the carrier substance will initially be fluid, most preferably liquid, to allow for its introduction by injection. Upon introduction into the fallopian tubes or shortly thereafter, it will set up as a gel.

Since the active chemical agents to be used with the carrier substance for forming the compositions described herein are described in detail within the literature and are well known in the art, only some of the more typical active chemical agents will be enumerated hereinbelow with the understanding that substantially all of the prior fibrous tissue growth promoting agents of the prior art known for use in sterilization by blockage of the fallopian tubes can be utilized in combination with the carrier substances disclosed herein within the concept of the invention. That is, the list which follows is not intended to be exclusive but is merely to be illustrative of those tissue active agents which have found the greatest acceptance by previous investigators and which particularly lend themselves to the present invention. Among the preferred active agents are:

Silver nitrate or other silver salts such as silver acetate and silver lactate.
Formaldehyde
Sodium morrhuate
Quinacrine (and its salts such as quinacrine hyrochloride).
Methylcyanoacrylate powder in cured form
Iodine in complexes such as polyvinyl-pyrollidone As noted, the above list is by no means inclusive as to all of the possible operable tissue active agents. The anion of the silver salts may be other than the nitrate. Soluble as well as insoluble salts are usable. The principal restriction is that the salts or other tissue active chemical materials that are utilized must be present in effective amounts to not only bring about the desired fibrous tissue growth within the fallopian tube to block same, ie., a blocking growth, but also must be a material which is not systemically poisoning to the subject. That is, the agent must be capable of causing the fibrous tissue to form but it must not effect the body generally. It must have only the desired local effect. Also, the agent must be eliminated from the body, usually gradually with time. This may be by bio-degradation, absorption, metabolization or the like. Consequently, the agent must be generally biologically compatible except for the desired local effect. The effective amounts required will vary depending on the particular agents or agents selected. For example. in the case of silver nitrate, at least about 5% by weight must be used to cause closed scarring. Lesser amounts become less effective until at 2.5% by weight the agent is completely ineffective.

EXAMPLES—I

As previously stated, a wide variety of gel forming agents can be utilized as the carrier for the tissue active chemical material. One of the preferred gels in accordance with the invention is a gel material formed of polyoxypropylene-polyoxyethylene block copolymer condensates having a molecular weight in the range of about 9,760 to about 13,200. These materials are well known in the art and are available commercially under the tradename Pluronic from Wyandotte Corporation of Wyandotte, Mich. It has been found that the Pluronic material sold by Wyandotte under their trade designation F-127 is particularly useful is the present invention. When solutions are prepared of about 20% by weight Pluronic F-127 with water, the resulting solution is liquid at temperatures below about 22°-25° C. and becomes a gel at temperatures below about 22°-25° C. and becomes a gel at temperatures in excess of 25° C. This constitutes a highly desirable substance as the carrier for the tissue active chemical. It is preferred in that it is liquid at the normal room temperatures and sets up and becomes a gel under the simplest and most certain procedure of merely encountering the elevated temperatures of the human body (37° C.). The Pluronics have a long history of use as a carrier agent in both the cosmetic and pharmeceutical industries. They are gradually absorbed or degraded by exposure of the body tissue so that with passage of time they are entirely eliminated by the body's own mechanism. In all of the instances of use of gels in accordance with the invention, it will be found that the gel as well as the chemical active agent is eliminated with time by the body. The precise mechanism by which elimination takes place is not known for each of the gels and chemicals but generally may be classified as either bio-degrading, metabolizing, or by absorption.

EXAMPLES—Ia

The specific utilization of the Pluronic F-127 is illustrated by a solution consisting of 20 grams by weight of the polymer F-127 in 80 grams by weight of water. To this solution is added in quantities ranging from about 5% up to about 20% by weight of the total of gel agent and water, a silver salt, such as silver nitrate. The lesser quantity of silver nitrate is preferred although the high concentrations can be utilized. Quantities of silver nitrate less than about 5% by weight are increasingly less effective as a scarification agent for fallopian tube tissue and are completely ineffective at 2.5%. There is an effect on the gelling properties resulting from inclusion of the silver nitrate or other silver salts. As the quantity of salt increases it may require slightly larger amounts of F-127 to bring about gelation at the desired temperature. The gel in accordance with this formulation is distinctly liquid at 20° C. and begins to form a gel at about 22° C. A relatively strong gel structure is achieved at temperatures in excess of 25° C. and by the time that the body temperature of 37° C. is reached, a very pronounced gel structure is achieved. This material in the liquid stage may be employed within an apparatus such as that described in the Bolduc U.S. Pat. No. 3,822,702, for injection into the uterine cavity and then into the fallopian tubes. The mixture is substituted for the methylcyanoacrylate material as taught in the patent and injected under substantially the same procedure so that it is placed into the fallopian tube and occupies a significant portion of the total length of the fallopian tube. It is important that the agent in accordance with the invention occupy a substantial length of the fallopian tube as the epithelial tissue of the fallopian tube repairs itself by growing in from both ends of the injected material. Scarring of the tissue of the fallopian tube to bring about closure is accomplished by promotion of growth of fibroblastic tissue in the region occupied by the injected material at a rate that is faster than a regrowth of the destroyed tissue. By occupying a significant portion of the length of the fallopian tube, the gels and sclerosing agents in accordance with the invention accomplish blockage by the growth of the fibrous tissue at a rate faster than the epithelial tissue regrows and thus closure is accomplished.

It will of course be recognized that the formulation given above for the gel forming carrier is only illustrative and that gels may readily be formulated with greater or lesser amounts of Pluronic F-127 than the examples given above and still be within the scope of the invention. For example, if the amount of F-127 is increased above 20% by weight in water, the gel formation will take place at lower temperatures than those indicated. If a lesser quantity of F-127 is used, a somewhat higher temperature is required to produce gelling. The critical point of the invention in the form of the "increased temperature produced gel" is that the carrier substance must produce a gel at the normal body temperature of the subject.

EXAMPLES—Ib

Also, While the invention has been specifically described in connection with silver nitrate as the tissue active chemical, it will be understood that the whole gamut of tissue active chemicals used by the prior art, including those listed above, may be utilized. For illustration purposes, the concentration of the tissue active chemicals may desirably be as follows for gel forming materials of this class.

Formaldehyde:5–20% by weight
Sodium morrhuate:5% by weight
Quinacrine (quinacrine hydrochloride saturated solution plus a small amount of quinacrine to insure saturation) 10% by weight
Powdered polymerized methylcyanoacrylate 10% by weight Pluronic F-127 can be dispersed in formaldehyde solutions as concentrated as 25% (formaldehyde), and in silver salt solutions of up to 20% silver nitrate for example (about 13% with respect to the silver ion) without a significant effect upon the gel/temperature relationship of the dispersion. The Pluronic concentrations as high as 26% were prepared successfully.

5%–20% formaldehyde/22% Pluronic dispersions and 5%–15% silver nitrate/22% Pluronic dispersions were tested satisfactorily.

EXAMPLES—Ic

Another example of a gel forming agent useful in this class of materials is a derivative of metal cellulose called Methacel. This material is available from Dow Chemical Company of Midland, Mich. This substance chemically is hydroxypropylmethyl cellulose. The concentration of this material required to produce a satisfactory gel for purposes of the invention is preferably from about 0.5 to 3% by weight of Methacel in water. Again, the tissue fibrosing agents are preferably included in the gel substance in the concentration levels referred to above.

EXAMPLES—II

Gels may also be used as the carrier medium for the tissue active chemicals that are formed during a cooling cycle. That is, one may produce a solution of the active chemical agent in a gel forming carrier that is fluid at a temperature somewhat above body temperature, at least about 20° C. above body temperature being preferred, but which forms a gel by the lowering of the temperature to substantially that of the body. Generally, the temperature of the solution carrier that forms the gel should be under about 51° C. at the time of injection into the fallopian tubes with gelation occurring at about 10° C. above the body temperature. The concentration and selection of an active substance may be in accordance with the procedures and materials described above. Many gel forming agents fall within this class. As examples of such agents, one may use materials as listed below.

EXAMPLES—IIa

Agar in a concentration of 1–3% by weight in water produces a gel which will melt at about 99° C. and upon cooling regels at about 39° C. This gel and any one of the tissue fibrosing agents in the concentration indicated above is injected at about 49° C. or less into the fallopian tubes in the manner described previously. On further cooling to a body temperature, the gel forms and will remain a gel even though the temperature is raised above normal body temperatures of 37° C. In fact, the gel will not redissolve until a temperature of nearly 99° C. is again attained. The gel acts to hold the tissue fibrosing agent in place in the same manner as those described previously.

EXAMPLES—IIb

Furcelleran is a seaweed extract which has similar properties to those of agar. In concentration of about 0.2% of a solution in water, a gel is formed which melts at about 80° C. and goes into solution. On cooling, the gel reforms at about 40° C. As in the case of agar, the tissue fibrosing additives will be included in the quantities referred to above. In this example, as well as in the example of agar, the addition of the tissue fibrosing agents seem to have little effect on the gel properties.

EXAMPLES—IIc

Another example under this class of gel formers is the use of Polyethylene Glycol 1000 available from Polyscience Inc. of Paul Valley Industrial Park, Warrington, Pa. This material forms a gel at temperatures of 34–40° C. depending upon the concentrations of Polyethylene Glycol that are used.

EXAMPLES—III

The gel forming agents utilizable in the invention in accordance with this example include those which are initially solutions and which can be gelled through use of an additive such as a metal ion. As examples of this class of gelling agents, one may use materials such as those identified below.

EXAMPLES—IIIa

As one example, one may utilize a carboxymethylcellulose solution. This solution would include the active chemical agents as set out above. Either immediately prior to the injection procedure when the material was to be introduced into the fallopian tubes or simultaneously with such injection, the carboxymethyl cellulose solution with the active chemical agent would have introduced into it a quantity of aluminum ion or $Fe^{+3}$ ion or any trivalent metal ion that is non-toxic to bring about the desired gelling. Another similar reaction to produce gelling can be obtained utilizing alginates as the gel forming substance with the use of a metal ion gel former such as calcium ion to bring about the actual gelation. The calcium ion can be introduced either immediately preceding injection or simultaneously with the injection by suitable inter-mixing as the material is injected into the fallopian tube area.

EXAMPLES—IIIb

As examples illustrative of aginate gels, another preferred embodiment, a stock dispersion of sodium alginate was made up in the following manner: 2.0 gm of the alginate (KELCO-GEL LV trademark for a refined sodium alginate available from the Kelco Co., Division of Merck & Co., Inc., Box 23076, San Diego, Calif. 92123) was slowly added to 90 ml of distilled water warmed to 60–70° C. stirring continuously until the colloid was completely dispersed. The dispersion was cooled to room temperature and the volume brought to 100 ml with distilled water. STOCK #I.

A second stock dispersion was made up in the same manner except the solvent was a 4% formaldehyde solution. STOCK #II.

The test procedure was as follows: 2 ml of one of the alginate stock dispersions was put into one barrel of a twin-barrel syringe and 0.5 ml of a gelling agent, as specified for each of the examples below, was put into the other barrel. The syringe exits feed into a motionless mixer made by putting a series of deep indents along the length of a piece of glass tubing. All of the tests were carried out at room temperature; and all of the test systems gelled within one minute of mixing the alginate with the gelling agent.

EXAMPLES—IIIb.1

2 ml of stock #I and 0.5 ml of 4.43% calcium nitrate gelling agent in the form of a solution containing 10% silver nitrate as the tissue active agent were intimately mixed in the motionless mixer tube. A firm, slightly opalescent gel immediately formed. The same procedure was followed with the gelling agents 2% calcium glycero-phosphate, 4% calcium acetate, and 4% calcium lactate, all also containing 10% silver nitrate as the fibrous tissue growth promoting agent.

EXAMPLES—IIIb.2

The same as in Example IIIb.1 except the silver salt fibrous tissue growth promoting agent used in the gelling agent was silver acetate (10%).

EXAMPLES—IIIb.3

The same as in Example IIIb.1 but the gelling agent was a 10% ferric chloride solution containing in one instance 10% silver nitrate, in another 10% silver acetate, and another 12.6% silver lactate as the fibrous tissue growth promoting agent.

EXAMPLES—IIIb.4

The same as in Example IIIb.1 but the gelling agent was a 10% aluminum sulfate solution containing in one instance 10% silver nitrate, and in another 10% silver acetate, and in another, 12.6% silver lactate as the fibrous tissue growth promoting agent.

EXAMPLES—IIIb.5

The same as in Examples IIIb.1 to IIIb.4 except the alginate moiety was from stock #II.

Previous studies showed that the gellation velocity of these systems is essentially unaffected by the presence of either formaldehyde or any of the silver salts.

EXAMPLES—IIIc

Pectins may also be used as the gelling material with the use of a manganese sulfate alkaline solution as the gel promoting material.

EXAMPLES—IIId

Non-organic gelling agents may also be utilized such a sodium silicate solutions which are readily gelled by adjustment of the pH.

Of course, in all of the examples that have been given above and hereinbelow it will be recognized that the substance to be injected must be injected with care so as not to be forced into the peritoneal cavity or to bring about other damage of an undesired kind to the subject. This can readily be accomplished with personnel well below the skills of fully trained doctors through the use of apparatus such as described in the Bolduc Patent supra. Those solutions used in the forming of the gels and as carriers for the active chemical materials will of course be bacterially sterile and care will naturally be taken to insure that they do not become contaminated with the agents that could bring about an infection within the uterus.

EXAMPLES—IV

It is also contemplated that one may utilize as the carrier for the active chemical substance gels which under the influence of high sheer stresses are momentarily changed to fluid or fluid acting materials and are reconstituted as gels once the high sheer action is discontinued. For example, one may form the gel carrier and active chemical agent within the apparatus described in the Bolduc patent and by the use of sufficient shear stresses during the injection cycle this material will be at least momentarily converted to a fluid or semi-fluid acting medium. Internal shear stress of sufficient magnitude to temporarily liquify the gel as refined herein as predetermined internal stress. Liquification of the gel can be readily observed in practice to determine when the stress is adequate. Once the gelling material is positioned within the fallopian tube and the shear forces are no longer present, the gel structure is reconstituted and acts in accordance with the invention to retain the active chemical substance in the desired position for a period sufficient to bring about the fibrous tissue growth.

EXAMPLES—IVa

Examples of substances which show this property include carboxymethyl cellulose (CMC) in which the degree of substitution (D.S.) is on the order of 0.4; and sodium alginates, such as KELGIN-MV, trademark for a sodium alginate available from Kelco Co., Division of Merck & Co., Inc., 20 N. Wacker Drive, Chicago, Ill. 60606, above about 2% dispersion and PLURONIC F-127 dispersions above about 19% (19%–23%), between a temperature range of 20 to 37 deg.C. The shear rate required to break any of the pluronic gels is for example in the vicinity of 20 reciprocal seconds, a rate easily realized with the device described in the aforementioned Bolduc patent.

Numerous other materials will readily suggest themselves to the reader as coming within the scope of the concept of the invention. The important thing in the selection of the gelling agent is that it must be an agent which retains its gel structure for a sufficient period of time to insure the retention of active chemical agent within the fallopian tubes to bring about the fibrous tissue growth and yet must be one which is body compatible in being capable of maintaining its gel structure in the presence of the active chemical agents. The range of concentrations of the gelling agents needed to produce a gel upon treatment with the metal ions are well known in the art and will not be elaborated upon here. The important criteria are that the gel should be stable under body conditions and that the combined materials be non-systemically poisoning to the subject.

Various modifications of the precise teachings above will readily be apparent. For example, while all of the above examples have been described in connection with aqueous systems, there is no requirement that this be the case. Mixtures of water and alcohols plus a gelling agent can be used as the carriers so long as the required gel is produced in the fallopian tube. Completely non-aqueous systems are also possible. In this instance, the active chemical agent may be dispersed in the gel forming substance if it is not actually significantly soluble therein.

Also, the upper limits on the percentage ranges for the effective amount of fibrous tissue growth promoting agent is merely one of convenience for use. Larger amounts may be used but are not ordinarily necessary to cause blockage.

All percentages set forth herein are by weight unless indicated otherwise.

Having described the invention, the exclusive property rights therein are to be defined by the following claims.

What is claimed is:

1. The method of permanently sterilizing a female subject comprising:
   (a) disposing in the fallopian tubes of the subject a mixture of a carrier substance, which forms a gel in situ after being disposed in the fallopian tubes of the subject, and a quantity of fibrous tissue growth promoting agent being present in the mixture in a quantity sufficient to promote fibrous tissue growth and being non-systemically toxic to the subject, and
   (b) retaining said mixture therewithin while gelling of the carrier substance takes place.

2. The method in accordance with claim 1 wherein the carrier substance is a solution of water and a block polymer of polyoxypropylene-polyoxyethylene having a molecular weight of from about 9,760 to about 13,200, which is a liquid at temperatures below about 25° C. and becomes a gel at a temperature between about 25° C. and body temperature.

3. The method in accordance with claim 2 wherein the fibrous tissue growth promoting agent is silver ions in a quantity sufficient to promote fibrous tissue growth and above about 5% by weight.

4. The method in accordance with claim 2 wherein the fibrous tissue growth promoting agent is selected from the group consisting of silver salts, sodium morrhuate, quinacrine and its salts, formaldehyde and polymerized methylcyanoacrylate powder.

5. The method in accordance with claim 1 wherein said carrier substance is a solution of carboxymethyl cellulose and water and it is mixed with a solution containing a metal ion during disposal in the fallopian tubes to produce gelling of said carrier substance.

6. The method in accordance with claim 1 wherein the carrier substance is a mixture of water and a gel forming substance that is liquid at temperatures above the body temperature and forms a gel substantially at body temperature.

7. The method of sterilizing a female subject comprising:
   (a) injecting into a substantial length of the fallopian tubes of the subject, while in a fluid state and at a temperature below about 51° C., a mixture of (1) a carrier substance which forms a gel that is non-systemically toxic and which retains its gel structure in situ for a substantial period of time after being injected into the fallopian tubes of the subject and is eliminated by the body with time, and (2) a fibrous tissue growth promoting agent in sufficient quantity in said mixture to promote sufficient fibrous tissue growth within such fallopian tubes when so injected to thereby block the passages thereof before the carrier substance loses its gel structure and is eliminated by the body of the subject; and
   (b) retaining that mixture within that length of the fallopian tubes of the subject until gelling of the carrier substance of the mixture has taken place whereby the mixture is temporarily held in place.

8. The method in accordance with claim 7 wherein the carrier substance is a solution of water and a block polymer of polyoxypropylene-polyoxyethylene having a molecular weight of from about 9,760 to about 13,200 and which is a liquid at temperatures below about 25° C. and becomes a gel at a temperature between about 25° C. and below body temperature.

9. The method in accordance with claim 8 wherein the fibrous tissue growth promoting agent is silver ions in a quantity sufficient to promote fibrous tissue growth and in the range of about 5% to about 20% by weight of said carrier substance.

10. The method in accordance with claim 8 wherein the fibrous tissue growth promoting agent is selected from the group consisting of silver salts, sodium morrhuate, quinacrine and its salts, formaldehyde and polymerized methylcyanoacrylate powder.

11. The method in accordance with claim 7 wherein the mixture of said carrier substance and fibrous tissue growth promoting agent is a gel prior to injection into the fallopian tube and shear stresses are applied to said mixture during injection of a magnitude to momentarily fluidize said gel immediately prior to introduction into the fallopian tube.

12. The method in accordance with claim 7 wherein the carrier substance is a mixture of water and a gel forming substance that is liquid at temperatures above the body temperature and forms a gel substantially at body temperature.

13. The method of permanently sterilizing a female subject comprising:
   (a) disposing in the fallopian tubes of the subject a mixture of a gelled carrier substance and a fibrous tissue growth promoting agent, which at least temporarily is fluidized by application of shear stress thereto during introduction into the fallopian tubes, and
   (b) retaining said mixture therewithin for a time to promote fibrous tissue growth.

14. A composition for sterilizing a female subject by the introduction thereof into the fallopian tubes of the female subject, the composition comprising:
   (a) an in situ gel-forming carrier substance containing an alginate, and
   (b) a fibrous tissue growth promoting agent carried by the gel-forming carrier substance in an effective amount for causing the growth of blocking tissue in the fallopian tubes of the subject.

15. The composition according to claim 14 wherein the alginate is dissolved in water.

16. The composition according to claims 14 or 15 wherein the gel-forming substance also contains a gelling agent.

17. The composition according to claim 14 wherein the alginate is a sodium alginate.

18. The composition according to claim 15 wherein the gelling agent is selected from the group consisting of calcium nitrate, calcium glycero-phosphate, calcium acetate, calcium lactate, ferric chloride, aluminum sulfate and mixtures thereof.

19. The composition according to claim 16 wherein the gelling agent is selected from the group consisting of calcium nitrate, calcium glycero-phosphate, calcium acetate, calcium lactate, ferric chloride, aluminum sulfate and mixtures thereof.

20. The composition according to claim 14 wherein the fibrous tissue growth promoting agent is selected from the group consisting of silver salts, sodium morrhuate, quinacrine and its salts, formaldehyde, polymerized methylcyanoacrylate powder and mixtures thereof.

21. The composition according to claim 15 wherein the fibrous tissue growth promoting agent is selected from the group consisting of silver salts, sodium morrhuate, quinacrine and its salts, formaldehyde, polymerized methylcyanoacrylate powder and mixtures thereof.

22. The composition according to claim 16 wherein the fibrous tissue growth promoting agent is selected from the group consisting of silver salts, sodium morrhuate, quinacrine and its salts, formaldehyde, polymerized methylcyanoacrylate powder and mixtures thereof.

23. A composition in accordance with claim 14 wherein the tissue growth promoting agent is polymethylcyanoacrylate powder in a quantity of about 10% by weight of said carrier substance.

24. A composition for sterilizing a female subject by introducing into the fallopian tubes of the female subject a composition comprising an in-situ gel-forming carrier substance containing:
    (a) a gelling agent selected from the group consisting of calcium nitrate, calcium glycerophosphate, calcium acetate, calcium lactate, ferric chloride, aluminum sulfate and mixtures thereof, and
    (b) a fibrous tissue growth promoting agent carried by the gel-forming carrier substance in an effective amount for causing the growth of blocking tissue in the fallopian tubes of the subject.

25. The composition according to claim 24 wherein the fibrous tissue growth promoting agent is selected from the group consisting of silver salts, sodium morrhuate, quinacrine and its salts, formaldehyde, polymerized methylcyanoacrylate powder and mixtures thereof.

* * * * *

UNITED STATES PATENT AND TRADEMARK OFFICE
CERTIFICATE OF CORRECTION

PATENT NO. : 4,185,618
DATED : January 29, 1980
INVENTOR(S) : Harold Corey

It is certified that error appears in the above-identified patent and that said Letters Patent are hereby corrected as shown below:

Column 1, line 59, "therein" should be --herein--.

Column 3, line 13, "hyrochlo-" should be --hydrochlo--.

Column 3, line 35, "agents" first occurrence should be --agent--.

Column 3, line 57, delete "below about 22°-25°C and".

Column 3, line 58, delete "becomes a gel at temperatures".

Column 3, line 67, "of" should be --to--.

Column 5, line 55, after "active" insert --chemical--.

Column 7, line 56, "a" should be --as--.

Signed and Sealed this

Sixth Day of May 1980

[SEAL]

Attest:

SIDNEY A. DIAMOND

Attesting Officer    Commissioner of Patents and Trademarks